(12) United States Patent
Schneider et al.

(10) Patent No.: US 8,163,161 B2
(45) Date of Patent: Apr. 24, 2012

(54) GAS SENSOR AND METHOD FOR DETECTING PARTICLES IN A GAS FLOW

(75) Inventors: Jens Schneider, Leonberg (DE); Detlef Heimann, Gerlingen (DE); Goetz Reinhardt, Boeblingen (DE); Henrico Runge, Stuttgart (DE); Lothar Diehl, Gerlingen (DE); Juergen Ruth, Stuttgart (DE); Thomas Seiler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 607 days.

(21) Appl. No.: 12/277,952

(22) Filed: Nov. 25, 2008

(65) Prior Publication Data
US 2009/0152130 A1    Jun. 18, 2009

(30) Foreign Application Priority Data
Nov. 28, 2007 (DE) .......................... 10 2007 057 135

(51) Int. Cl.
*G01N 27/407* (2006.01)
(52) U.S. Cl. ...................................... 205/781; 205/785
(58) Field of Classification Search .......... 204/421–429; 205/781, 783.5, 784.5, 785; 73/31.05, 114.72, 73/114.73
See application file for complete search history.

(56) References Cited

U.S. PATENT DOCUMENTS
6,401,522 B1 *  6/2002  Kon et al. ................. 73/31.05

FOREIGN PATENT DOCUMENTS
| DE | 197 44 579 | 4/1998 |
| DE | 100 48 240 | 4/2002 |
| DE | 101 21 771 | 11/2002 |

* cited by examiner

*Primary Examiner* — Kaj K Olsen
*Assistant Examiner* — Kourtney R Salzman
(74) *Attorney, Agent, or Firm* — Kenyon & Kenyon LLP

(57) ABSTRACT

A gas sensor for detecting particles in a gas stream has a first electrochemical pump cell, which has a measuring chamber in which a first electrode is disposed to pump particles between the first measuring chamber and the gas stream. Furthermore, a second electrochemical pump cell is provided, which has a second measuring chamber in which a second electrode is disposed so as to pump particles. The second measuring chamber is connected to the gas stream via an absorber medium for absorption of the particles to be detected. This makes it possible to absorb the particles to be detected in a first operating mode using the absorber medium, and to desorb the absorbed particles in a second operating mode, and to detect the quantity of the desorbed particles. Thus, the gas sensor is able to take even low concentrations into account, and short-term measuring errors do not have such a serious effect.

2 Claims, 1 Drawing Sheet

GAS SENSOR AND METHOD FOR DETECTING PARTICLES IN A GAS FLOW

RELATED APPLICATION INFORMATION

The present application claims priority to and the benefit of German patent application no. 102007057135.8, which was filed in Germany on Nov. 28, 2007, the disclosure of which is incorporated herein by reference.

FIELD OF THE INVENTION

The present invention relates to a gas sensor and to a method with whose aid particles, in particular gaseous components and/or molecules, in a gas stream, especially in nitrogen oxides ($NO_x$) in an exhaust-gas stream of a motor vehicle are able to be detected.

BACKGROUND INFORMATION

German patent document DE 10 2005 056 522 A1 discusses a gas sensor, which operates according to the double chamber principle and has two electrochemical pump cells, each of which has an electrode disposed in a measuring chamber with whose aid gas molecules can be pumped between the measuring chamber and the environment. The first pump cell is connected to the gas stream in order to detect the particles to be detected in the gas stream. The second pump cell is connected as reference to a reference-gas stream, which in principle contains no particles to be detected. The electrodes of the pump cells each cooperate with an antipolar counter electrode assigned to them, so that it is possible to tap a measuring signal, in particular an electric current, at the individual electrodes. The ratio of the measuring signal received from the first electrode and the reference measuring signal received from a second electrode is a measure for the concentration of the particles to be detected, in particular $NO_x$.

A disadvantage of such a gas sensor is that especially very low concentrations are unable to be detected because such measuring signals are lost in the signal noise. In particular, such measuring signals cannot be differentiated from possible interference resulting, for instance, from instabilities or electric incouplings. Furthermore, it is possible that the measuring signal changes due to aging manifestations of the gas sensor, this change of the measuring signal being unable to be considered in the concentration measurement.

SUMMARY OF THE INVENTION

It is an object of the present invention to provide a gas sensor as well as a method for detecting particles in a gas stream, which are able to consider even low concentrations and are more robust with respect to short-term measuring errors.

According to the present invention, the object is achieved by a gas sensor having the features described herein, and by a method for detecting particles in a gas stream having the method features described herein. Advantageous developments of the present invention are also described herein.

The gas sensor according to the present invention for the detection of particles in a gas stream, with whose aid $NO_x$ in particular is able to be detected in an exhaust-gas stream of a motor vehicle, has a first electrochemical pump cell and a second electrochemical pump cell. The first electrochemical pump cell has a first measuring chamber inside which a first electrode is disposed. With the aid of the first pump cell it is possible to pump particles between the first measuring chamber and the gas stream. In other words, particles are able to be pumped from the gas stream into the measuring chamber and/or from the measuring chamber into the gas stream. In a corresponding manner, the second pump cell has a second measuring chamber, in which a second electrode is disposed. Using the second pump cell it is possible to pump particles between the measuring chamber and an environment. According to the present invention, the second measuring chamber is connected to the gas stream via an absorber medium for absorption of the particles to be detected. In particular, a mass flow of the gas stream into the second pump cell may take place exclusively only via the absorber medium.

By disposing the absorber medium between the second measuring chamber and the gas stream, it is prevented that the particles to be detected, such as gaseous components and/or molecules, for example, may reach the second measuring chamber, so that the second pump cell is able to form a reference for the first pump cell. At the same time, the particles to be detected and contained in the mass flow flowing from the gas stream into the second measuring chamber gradually accumulate in the absorber medium. The particles accumulated in the absorber medium may be removed from the absorber medium after a specific time interval, for instance by heating the absorber medium to a high temperature such that the previously adsorbed particles are desorbed from the absorber medium. The desorbed particles can then be detected by an additional pump cell, for instance. The detection of the desorbed particles may take place with the aid of the second pump cell, which is provided in the gas sensor anyway. The desorbed particles have a high concentration such that they are measurable without significant problems, so that no loss of information due to signal noise has to be expected. Since the quantity of the desorbed particles corresponds to the absolute quantity of the particles absorbed over a specific period of time, a measuring signal is able to be obtained that represents a measure for the accumulated quantity of the particles to be detected within a specific period of time. In comparison with a continuous measurement, short-term measuring errors are unable to affect the measuring results to any significant extent, so that the gas sensor according to the present invention is more robust with respect to short-term measuring errors. It is possible, in particular, to compare the measurement of the accumulated desorbed particles with the continuous measurement in order to subject the previously obtained measuring results to a plausibility check. This allows faulty measurements to be identified and the forwarding of faulty measuring results to be prevented and/or corrected.

A heating device may be provided to heat the first pump cell and/or the second pump cell. The heating device is thermally connected to the absorber medium especially in such a way that a first temperature $T_1$ and a second temperature $T_2$ that differs from first temperature $T_1$ is able to be set in the absorber medium with the aid of the heating device. At the first temperature $T_1$, the absorber medium absorbs the particles to be detected, while at second temperature $T_2$ the absorber medium desorbs the previously absorbed particles to be detected. Depending on the operating mode of the heating device, the absorber medium may be heated or cooled at a specific predefined instant or within specific predefined time intervals, in order to bring the absorber arrangement (means) into a condition in which the absorber medium absorbs or desorbs the particles to be detected. The absorber arrangement (means) is heated to second temperature $T_2$ especially at an instant before the absorption capacity of the absorber medium is exhausted. This prevents imprecise measuring results. In an exemplary manner, a safety circuit may be provided, which switches the heating device on so as to heat the absorber medium to second temperature $T_2$ if a particle to be detected is determined within the second pump cell. This makes it possible to avoid excessive time intervals within which the absorber medium collects the particles to be detected. Instead, depending on the instantaneous concentration of the particles to be detected, it is possible to adapt the time intervals and, if required, to shorten them in the case of excessive concentrations.

In an exemplary manner, a memory unit may be provided, with whose aid the time characteristic of the measuring signals able to be obtained from the first electrode and the second electrode may be stored. In addition, it is possible to provide a comparison unit, with whose aid the time characteristic of the received measuring signals for a first operating mode, in which the absorber medium absorbs the particles to be detected, is compared to the time characteristic of the arriving measuring signals for a second operating mode, in which the absorber medium desorbs the absorbed particles to be detected. In this way the measured values continuously measured in the first operating mode can be compared to the aggregate quantity of the desorbed particles in the second operating mode. Furthermore, different measuring cycles are able to be compared to each other in order to determine, for example, longer-term trends that point to a gradual impairment of a catalytic converter of a motor vehicle, for instance.

In an exemplary development, a discharge channel, which is disposed at a distance to the absorber medium, may be in connection with the second measuring chamber. In particular, the discharge channel may be connected to a vacuum pressure source. This ensures that all particles desorbed from the absorber medium are pumped or aspirated into the second measuring chamber, so that faulty measuring values are avoided or reduced.

The first measuring chamber may be connected to the gas stream via a first supply channel. Analogously, the second measuring chamber may be connected to the gas stream via a second supply channel. The first supply channel and the second supply channel may have different cross sections, in particular, so that it is possible to specify an initial basic relationship of the measured values obtained from the first electrode and the second electrode via the selection of the cross sections of the supply channels. Depending on the selected cross section for the individual supply channel, a stronger or weaker signal is able to be obtained at the particular electrode of the pump cell.

The first measuring chamber may be connected to the gas stream via a first gas barrier in order to reduce a pumped mass flow. In addition or alternatively, the second measuring chamber may be connected to the gas stream via a second gas barrier so as to reduce a pumped mass flow. Depending on the size, the material, the porosity and comparable parameters, it is possible to control the gas stream pumped into the individual measuring chamber by the first gas barrier and/or the second gas barrier, so that an initial basic relationship of the measuring values obtained from the first electrode and the second electrode is able to be specified with the aid of the selection of suitable gas barriers, the first gas barrier and the second gas barrier having different capacities, in particular. In an exemplary manner, the second gas barrier may be formed by the absorber medium; in principle, it is of course possible to provide a further second gas barrier in addition to the absorber medium, in order to control the mass flow into the second measuring chamber.

The first electrode and the second electrode may cooperate with a shared antipolar counter electrode, so that there is no need to provide an individual counter electrode for each electrode. The counter electrode is exposed to the gas stream, in particular, in order to provide sufficient pumping action in the pump cells. Since the first pump cell and the second pump cell are each meant to detect the same particles, both electrodes are designed as cathode or anode, so that a shared counter electrode in the form of an anode or cathode is possible.

It is possible, in particular, for the first pump cell to have essentially the same design as the second pump cell, so that substantially identical component modules may be used to form the gas sensor. The first electrode and the second electrode may be made of the same material, such as gold-doped metal or rhodium-doped metal. The first electrode and the second electrode may have the same form. This makes it possible to reduce the number of different components, which simplifies the production.

Furthermore, the present invention relates to a gas sensor for detecting particles, in particular $NO_x$, in a gas stream, using precisely one electrochemical pump cell, which has a measuring chamber with an electrode. With the aid of the first pump cell particles are able to be pumped between the measuring chamber and the gas stream. According to the present invention, the measuring chamber is connected to the gas stream via an absorber medium for the absorption of the particles to be detected. As described above, the gas sensor may be configured and developed such that only a single measuring chamber is provided. As described before, this gas sensor is able to consider even low concentrations, thereby making the gas sensor more robust with respect to short-term measuring errors.

Furthermore, the present invention relates to a method for detecting particles, in particular NOx, in a gas stream, in which first a gas sensor, which is exposed to the gas stream, is provided. In particular the gas sensor may be designed or refined further as described above. A portion of the gas stream is pumped into the first measuring chamber with the aid of the first pump cell in order to obtain a first measuring signal. In addition, a portion of the gas stream is pumped into the second measuring chamber with the aid of the second pump cell in order to obtain a second measuring signal. Before the pumped mass flow enters the second measuring chamber, the pumped mass flow initially passes the absorber medium. At first, the second pump cell is operated at a first temperature $T_1$ in a first operating mode, at which the absorber medium absorbs the particles to be detected. Then the second pump cell is operated in a second operating mode at a second temperature $T_2$, at which the absorber medium desorbs the previously absorbed particles to be detected. This makes it possible in the second operating mode to measure the aggregate quantity of the previously absorbed particles to be detected, so that even low concentrations are able to be taken into account. Moreover, the effect of short-term measuring errors is reduced, which makes the method more robust. The changeover from the first operating mode into the second operating mode takes place especially before the absorption capacity of the absorber medium has been exhausted. The changeover from the second operating mode into the first operating mode takes place especially when virtually the entire previously absorbed quantity of the particles to be detected has been desorbed and, in particular, when the second pump cell no longer detects any particles to be detected and/or detects only the same number of particles as in the first pump cell.

In an especially particular manner, the time characteristic of the old measuring signals for the first operating mode may be compared to the time characteristic of the old measuring signals for the second operating mode. This makes it possible to detect measuring errors.

In the following text, the present invention is explained in greater detail with reference to the appended drawing with the aid of the exemplary embodiments.

DETAILED DESCRIPTION

Figure 1:
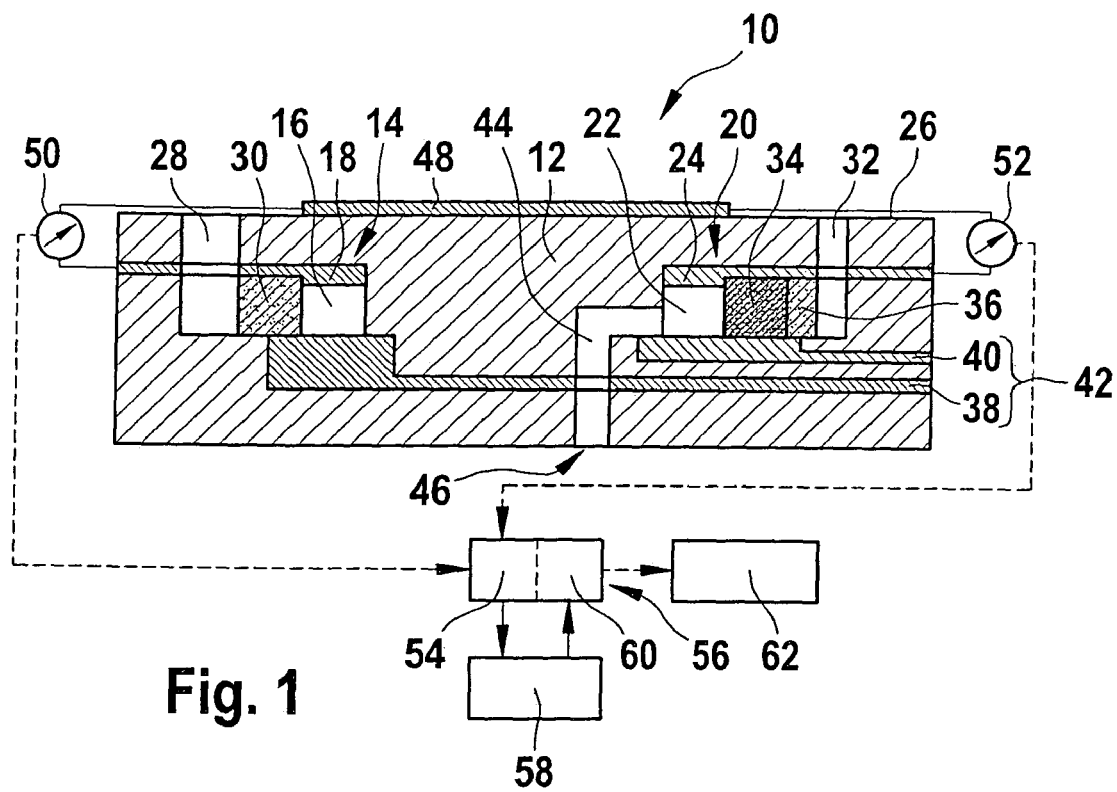
FIG. 1 shows a schematic view of the gas sensor according to the present invention.

Gas sensor 10 shown in FIG. 1 has a body 12, which usually has multiple layers, the multiple layers of body 12 not being shown in FIG. 1 for reasons of clarity. Inside body 12 of gas sensor 10 there is a first electrochemical pump cell 14, which has a measuring chamber 16 into which a first electrode 18 projects. In addition, a second electrochemical pump cell 20 is provided, which has a second measuring chamber 22 into which a second electrode 24 projects. Via an upper side 26, body 12 of gas sensor 10 is exposed to a gas stream whose $NO_x$ concentration, for example, is to be measured. To this end, first measuring chamber 16 is connected to the gas stream via a first supply channel 28. Disposed in front of first measuring chamber 16 is a first gas barrier 30, so that the mass flow pumped into first measuring chamber 16 via first supply channel 28 is able to be limited. In the illustrated exemplary embodiment, second measuring chamber 22 is connected to the gas stream via a second supply channel 32. However, the connection of second measuring chamber 22 to the gas stream takes place only via an interposed absorber medium 34 with whose aid the particles to be detected are able to be absorbed. In the event that the effect of absorber medium 34 as gas barrier is insufficient, a second gas barrier 36 may be provided, which could be placed upstream and/or downstream from absorber medium 34.

First pump cell 14 is able to be set to a specific temperature with the aid of a first heating element 38. Analogously, with the aid of a second heating element 40, second pump cell 20 is likewise able to be set to a specific temperature, which may be independent of the temperature set in first pump cell 18, in particular. The two heating elements 38, 40 may be part of the same heating device 42 or, for example, be connected to an energy source via a shared collective line. Using second heating element 40 of heating device 42, it is possible to heat and/or cool second pump cell 20 and absorber medium 34, in particular. As a result, absorber medium can be set to a first temperature $T_1$ at which absorber medium 34 absorbs the particles to be detected in a first operating mode. Following a suitable time interval and using a second heating element 40, a second temperature $T_2$ is able to be set in second pump cell 20 and in absorber medium 34, in particular, at which the previously absorbed particles to be detected are desorbed in a second operating mode. The desorbed particles can then be detected in second pump cell 20. To prevent a portion of the desorbed particles from making its way from absorber medium 34 via second supply channel 32 along second electrode 24 of second pump cell 20, a discharge channel 44 is provided, which points away from the gas stream and which routes the desorbed particles out of second measuring chamber 22 in the illustrated exemplary embodiment. Discharge channel 44 may be connected to a vacuum-pressure source for this purpose, the necessary vacuum pressure also being able to be implemented by the gas stream passing along an outlet opening 46 of discharge channel 44. An electron delivery or an electron acceptance takes place by a catalytic reaction of the particles to be detected at the surface of the particular electrode 18, 24, so that a current flows between the particular electrode 18, 24 and a corresponding antipolar counter electrode 48. In the illustrated exemplary embodiment, precisely one shared counter electrode 48 is provided for first electrode 18 and for second electrode 24. The current flowing between first electrode 18 and counter electrode 48 is able to be measured by a measuring device 50. In a corresponding manner, the current flowing between second electrode 24 and counter electrode 40 is measured by a second measuring device 52.

The measuring signals measured with the aid of measuring devices 50, 52 may be stored in a first part 54 of a memory unit 56, so that the time characteristic of the measuring signals remains stored. The stored measuring signals and, in particular, the relationship of the measured currents of different time periods, may be compared to each other in a comparator unit 58 connected to memory unit 56. In particular the relationship of the currents during the first operating mode measured by measuring devices 50, 52 are compared to the corresponding measuring signals during the second operating mode, so that it is possible to compare the aggregate quantity of the absorbed particles to be detected that are released by the absorber medium in the second operating mode, to the quantity of the particles to be detected in the first operating mode and continuously measured by first pump cell 14. The result of this comparison is able to be stored in a second part 60 of memory unit 56. In the event that no faulty measurement was determined on the basis of the comparison, then the result thus verified can be forwarded to, for example, an onboard unit 62 of a motor vehicle for further processing.

Figure 2:
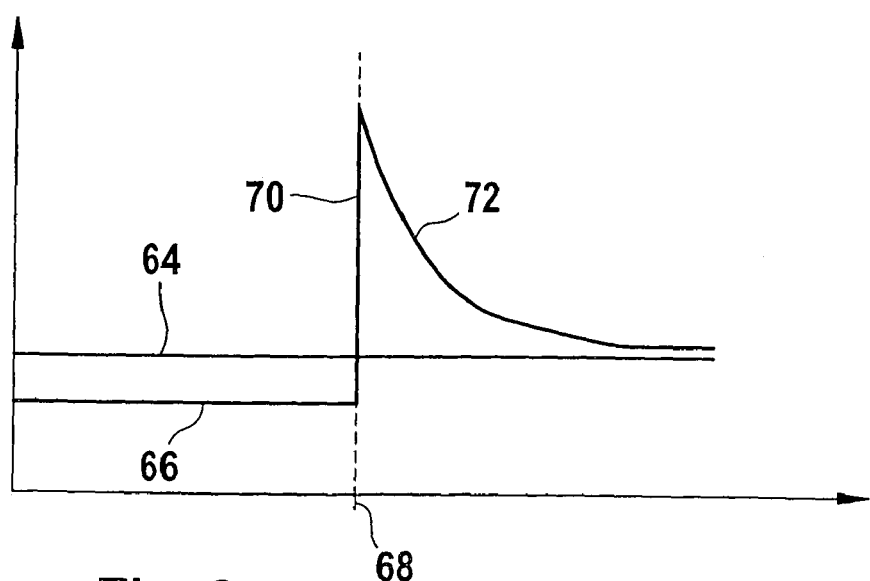
FIG. 2 shows a schematic diagram of qualitative measuring values when using the method according to the present invention.

In FIG. 2, the characteristic of the relationship of the currents measured by second measuring device 52 in relation to the currents measured by first measuring device 50 has been schematically plotted over the time. A normal line 64 indicates the characteristic when the gas stream does not include any particles to be detected. If the gas stream contains a constant concentration of the particles to be detected, then a characteristic 66 results because a larger flow than in second pump cell 20 is measured in first pump cell 14. If a changeover is made at an instant 68 from the first operating mode to the second operating mode and absorber medium 34 desorbs the previously absorbed particles, then an abrupt change 70 results because a considerably higher flow is suddenly able to be measured in second pump cell 20. In the second operating mode, a characteristic 72 comes about, which gradually drops since the quantity of the desorbed particles decreases as time passes. As soon as characteristic 72 approaches normal line 64, essentially all particles previously absorbed in absorber medium 34 are desorbed, so that gas sensor 10 may be operated in the first operating mode again.

The characteristic of the measured values illustrated in FIG. 2 corresponds to a measurement of particles that are able to be reduced. If oxidizable particles are measured by first measuring device 50 and/or second measuring device 52, then the particular characteristic may be represented in mirrored fashion at normal line 64.

To allow $NO_x$ to be measured using gas sensor 10, absorber medium 34 in particular consists of $BaCO_3$ or $BaO$, which is doped with a metal from the platinum group, in particular (Pd, Pt, Rh, Ru, Ir). Furthermore, first electrode 18 and second electrode 24 are operated as cathode, so that counter electrode 48 is operated as anode.

In an additional specific development (not shown), first pump cell 14 and its heating element 38 can be omitted. In this specific development, gas sensor 10 is essentially made up of only a single electrochemical pump cell 20, which may be designed like second pump cell 20 described earlier, i.e., in which the ambient gas reaches electrode 24 via an absorber medium 34. Used as signal to be analyzed is the comparison of the measured currents of this one pump cell 20 in the first operating mode to its measured currents in the second operating mode. The expected signal characteristic essentially corresponds to that in FIG. 2. In order to keep fault influences to a minimum, with the aid of an oxygen sensor likewise provided in the exhaust tract, a Lambda=1 exhaust gas may be set prior to the start of the signal recording, which is kept constant until the end of the second operating mode. This procedure may also be used for gas sensor 10 described first.

What is claimed is:

1. A method for detecting particles of $NO_x$ in a gas stream, the method comprising:
    providing a gas sensor and exposing it to the gas stream for detecting the particles in the gas stream, the gas sensor including a first electrochemical pump cell, which has a first measuring chamber including a first electrode, for pumping the particles between the first measuring chamber and the gas stream, and a second electrochemical pump cell, which has a second measuring chamber having a second electrode, for the pumping of the particles, wherein the second measuring chamber is connected to the gas stream via an absorber medium for absorption of the particles to be detected, the absorber medium being distinct from the first electrode and the second electrode;
    pumping a portion of the gas stream into the first measuring chamber with the first pump cell to obtain a first measuring signal;
    pumping a portion of the gas stream into the second measuring chamber with the second pump cell to obtain a second measuring signal, the pumped mass flow passing the absorber medium before entering the second measuring chamber;
    operating the second pump cell in a first operating mode at a first temperature, at which the absorber medium absorbs the particles to be detected; and
    subsequently operating the second pump cell in a second operating mode at a second temperature, at which the absorber medium desorbs the previously absorbed particles to be detected.

2. The method of claim 1, wherein a time characteristic of the received measuring signals for the first operating mode is compared to a time characteristic of the received measuring signals for the second operating mode.

* * * * *